United States Patent [19]

Fletcher, III

[11] Patent Number: 4,459,199
[45] Date of Patent: Jul. 10, 1984

[54] RUGGEDIZED ION-RESPONSIVE ELECTRODE AND ITS MANUFACTURING PROCESS

[75] Inventor: Kenneth S. Fletcher, III, Rehoboth, Mass.

[73] Assignee: The Foxboro Company, Foxboro, Mass.

[21] Appl. No.: 451,988

[22] Filed: Dec. 21, 1982

[51] Int. Cl.³ ............................................. G01N 27/36
[52] U.S. Cl. .................................. 204/420; 204/415; 204/419; 29/592 R
[58] Field of Search ...................... 204/420, 419, 415; 29/592 R

[56] References Cited

U.S. PATENT DOCUMENTS

| 2,117,596 | 5/1938 | Bender et al. | 204/420 |
| 3,582,474 | 6/1971 | Hair et al. | 204/420 X |
| 3,607,702 | 9/1971 | Haller | 204/416 |
| 3,717,565 | 2/1973 | Doyle | 204/195 M |
| 3,855,098 | 12/1974 | Fletcher | 204/195 G |

FOREIGN PATENT DOCUMENTS 495303 11/1938 United Kingdom .

Primary Examiner—G. L. Kaplan
Assistant Examiner—Nam X. Nguyen
Attorney, Agent, or Firm—Jack H. Wu

[57] ABSTRACT

An ion-sensitive electrode, usable for measuring the activity or concentration of a predetermined ion in a fluid stream of an industrial process, includes a vessel partially filled with an electrolyte and fabricated with one wall portion thereof comprising a rigid, porous fritted back-up element and a relatively thin, ion-sensitive, non-porous membrane. Being preferably made of the same ion-sensitive material as the membrane, the back-up element is produced using a sintering process which results in a porous solid having maze-like passages extending randomly therethrough in all directions. One surface of the back-up element is fused to and supports a thin layer of ion-sensitive material that has been applied to the back-up element, heated to its molten working temperature and then cooled to form the non-porous membrane. Located within the vessel, the back-up element also serves to transport the electrolyte through its passages for wetting the interior surface of the thin membrane fused to the back-up element. The exterior surface of the membrane is in contact with the fluid stream so that an electrical potential responsive to the activity or concentration of the pre-determined ion can be developed across the membrane.

10 Claims, 3 Drawing Figures

RUGGEDIZED ION-RESPONSIVE ELECTRODE AND ITS MANUFACTURING PROCESS

BACKGROUND OF THE INVENTION

1. Field

This invention relates to ion-sensitive electrodes for measuring ionic activity or concentration and, more particularly, to an electrode having substantial strength and ruggedness to facilitate use directly in industrial processes.

2. Description of the Prior Art

Measurements of ionic activity (or concentration) have long been made by inserting into a test liquid a pair of electrodes at least one of which may be provided with a fragile membrane selectively responsive to the particular ion of interest. One common type of such measurement is that of hydrogen ion activity (pH), conventionally made by a pair of electrodes referred to respectively as a measuring glass electrode and a reference electrode. Such electrodes develop an electrical potential (emf) which is a function of hydrogen ion activity. This potential is detected by an amplifier which produces an output usable for driving an indicator or a controller device.

The glass electrode generally comprises a cylindrical tubular element of glass closed off at one end by a thin bulbous glass membrane formed of a special composition sensitive to hydrogen (or other) ions. The outer surface of this membrane is immersed in the test liquid and makes electrical contact therewith. Being within the tubular element and isolated from the test liquid by the membrane, an electrically-conductive buffered liquid (electrolyte) is used for wetting the inner surface of the glass membrane so that the electrical potential responsive to the ion activity of the test liquid can be developed across the membrane.

Immersed in the electrolyte is a circuit-completing internal element formed for example of silver/silver-chloride and connected to an output extending to one input terminal of an amplifier. The other amplifier input terminal is connected to the reference electrode. These two electrodes form, together with the test liquid, an electro-chemical cell which generates an electrical potential proportional to the hydrogen-ion activity. The individual glass or reference electrodes are at times referred to as "half cells."

Although conventional glass electrodes have been used successfully for many years in making laboratory measurements and the like, there have been problems in employing such electrodes widely in industrial process fluid flows containing hard solid particles. Because it is so thin, the glass electrode membrane is relatively delicate and thus its ability to withstand mechanical shock and other abuse is limited. Moreover, there are processes (such as food) where the use of these electrodes is generally obviated because broken glass fragments cannot be tolerated in the fluid streams of those processes. Accordingly, there is a need for a ruggedized glass electrode. But it should be explained that it is not possible simply to make the glass membrane more rugged merely by increasing its thickness, for a thick membrane would present too high an electrical resistance and measurement of the electrical potentials developed would not be possible with commercially available high input-impedance voltage-measuring equipment.

U.S. Pat. No. 3,717,565, issued on Feb. 20, 1973, to Doyle, and assigned to the present assignee, discloses a ruggedized measurement glass electrode which includes a homogeneous integral mass of ion-sensitive material that is joined to and forms the lower portion of a tubular container holding an electrolyte. The portion of the mass disposed within the container is a disc-shaped honeycomb member having holes extending downwards from openings formed on the top surface of the mass and terminating in blind ends that are positioned a short distance from the bottom surface of the mass. The top surface is arranged within the container to be exposed to the electrolyte and the bottom surface, being the outer bottom surface of the container, is exposed to a test solution or fluid stream having an unknown ion activity. The thickness of the regions between the ends of the holes and the bottom surface is sufficiently small so as to be equivalent to the thin ion-sensitive membrane of the previously described prior art electrode. Since the ion-sensitive material of the integral mass is non-porous, the holes allow the electrolyte to contact the blind ends thereof so that a measurable electrical potential across the regions can be generated responsive to the ion activity of the solution contacting the second surface of the mass.

However, fabrication of the glass electrode disclosed by the '565 patent requires painstaking drilling, molding and/or machining techniques along with expensive specialized equipment in order to produce sufficiently thin regions between the blind ends and the bottom surface of the integral mass. As a result of the above requirements, the costs of producing the electrode taught by the Doyle patent are prohibitive.

In U.S. Pat. No. 3,855,098, issued on Dec. 17, 1974, to the present inventor and assigned to the present assignee, there is disclosed another ruggedized electrode in which the integral mass taught by Doyle is replaced by an assembly made by fusing a thin ion-sensitive glass membrane to a surface of a mechanically rigid back-up member. The back-up member is made of an inert (i.e., not ion-sensitive) porous ceramic having a coefficient of thermal expansion substantially matching that for the membrane. This arrangement greatly reduces the production costs because conventional and less expensive fusing techniques can be used to join the thin membrane to the back-up member. Being porous, the back-up member permits the electrolyte to be transported therethrough for wetting the interior surface of the membrane so that measurable electrical potentials can be generated across the membrane.

The making of the electrodes taught by the '098 patent is relatively straightforward for electrodes with glass membranes having low thermal expansion characteristics (such as those for sodium ion-sensitive formulations). However, for electrodes made with glass membranes having large thermal expansion characteristics (such as those for hydrogen ion-sensitive glasses), problems have been encountered in fabricating electrodes that perform comparably and/or are as durable or reliable as the above-mentioned sodium ion-sensitive electrodes. In regard to hydrogen ion-sensitive electrodes, the thermal expansion characteristics of available ceramics no longer match those for hydrogen-sensitive membranes within the 2% figure mentioned in the '098 patent, so that the glazing procedure used to produce the comparable electrodes becomes very complex and difficult.

As a result of the above, there is still a need for pH glass electrodes which are ruggedized to withstand mechanical shock and physical abuse and are usable in industrial process streams for measuring the ionic activity or concentration of a wide range of prescribed ions.

SUMMARY OF THE INVENTION

The above-described limitations of the electrodes disclosed in the '565 and '098 patents and other prior art devices are overcome by the provision of a new and improved electrode made in accordance with the teachings of the present invention. Briefly described, the preferred embodiment of applicant's invention includes a tubular glass container holding an electrolyte, a thin ion-sensitive, non-porous membrane which is joined to the glass container for forming a bottom portion thereof, and a rigid, porous supporting element disposed in the container. One surface of the supporting element is fused to the thin membrane thereby supporting and mechanically strengthening the membrane so that it can withstand mechanical shock and physical abuse when used in hard-particulate fluid streams of industrial processes.

Being a fritted solid which is produced by a process to be discussed in a subsequent section of this application, the supporting element is made with a porosity that is generally predetermined so as to permit the electrolyte in the glass container to seep through the supporting element for wetting the interior surface of the membrane. Moreover, in the preferred embodiment of applicant's invention, the thin membrane and the supporting element are both made of the same ion-sensitive material. This arrangement avoids the previously-mentioned problems that arise in the '098 patent in relation to differences in thermal expansion characteristics. In other words, the present invention can be made without compromising the durability or performance thereof when a material having large thermal expansion coefficients is used for this thin, ion-sensitive membrane.

The above-described and other features and advantages of the present invention will be more fully understood from a reading of the ensuing description given with reference to the appended drawings.

DETAILED DESCRIPTION OF THE PREFERRED EMBODIMENTS

Figure 1:
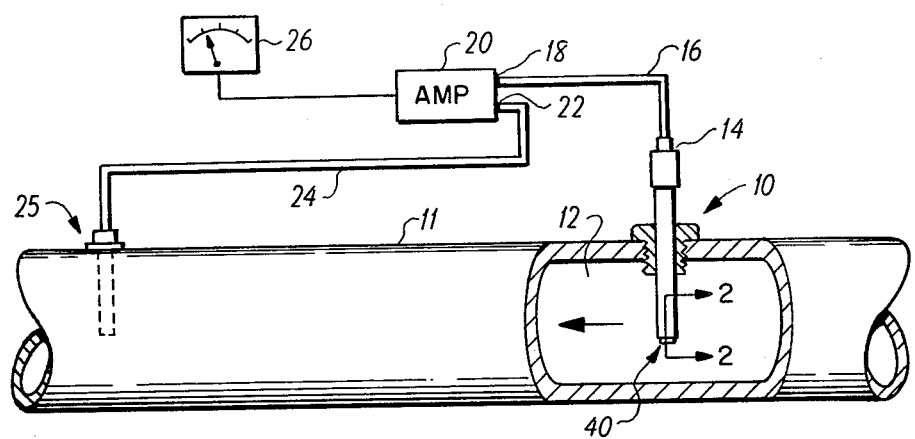
FIG. 1 is a partial sectional view showing a glass electrode embodying the present invention.

With reference to FIG. 1, there is shown in connection with an industrial process application a glass electrode 10 inserted in a pipe 11 to contact a stream of flowing liquid 12 (test solution) which has a hydrogen ion activity (pH) that is desired to be measured. The output terminal 14 of the electrode is connected in the usual fashion through a cable 16 to one input terminal 18 of an amplifier 20. The other input terminal 22 of this amplifier is connected by lead 24 to a conventional reference electrode such as a silver/silver-chloride cell 25 inserted into the flowing liquid 12 at a point spaced from the electrode 10. The output of the amplifier 20 drives an indicator or the like such as illustrated at 26.

Figure 2:
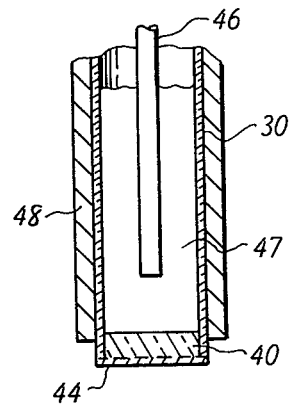
FIG. 2 is an enlarged detail section taken along line 2—2 of FIG. 1.

With reference also to FIG. 2, the glass electrode 10 comprises an elongated cylindrical tube 30, similar generally to the glass tubes used in conventional electrodes. The lower end of this tube is sealed off by a relatively thick and mechanically strong mass of porous material. The mass of material is in the form of a rigid supporting disk 40 dimensioned to fit closely within the end of the tube.

The supporting disk 40 is made by a fritting (or sintering) process wherein a compacted mass preferably of glass powder or fibers is heated in accordance with a predetermined time-temperature cycle. During heating the particles or fibers join together and produce a rigid body having a porosity that is a function of not only the size of the particles or fibers but also the specific time-temperature cycle used. The pores throughout the fritted solid form labyrinthine channels which extend randomly in all directions. Although they do not have the same dimensions throughout their entire paths, a large percentage of these paths will conform relatively closely to the size of the largest pore that is formed.

It should be understood that the fritted solid of supporting body 40 is not the same as the ceramic used for porous disk 32 of the '098 patent. In particular, the structure of the fritted solid is distinguishable from a ceramic because the homogeneous crystalline structure characteristic of a ceramic is not present throughout the mass of the fritted solid. Moreover, in the preferred embodiment where a glass material is used for supporting disk 40, another distinction exists because glass is known to have an amorphous structure and consequently is an entirely different class of material than a ceramic.

Using known technology to produce a sealed mechanical joint of substantial strength, the glass tube 30 is fused to supporting disk 40. The thermal expansion characteristics of both glass tube 30 and supporting disk 40 should be the same in order to insure that the joint therebetween can withstand relatively large changes during cooling and subsequent changes in ambient temperature when the device is ultimately used. For some applications, the glass tube 30 and supporting disk 40 may be made of identical material.

The outer (lower) surface of supporting disk 40 carries an extremely thin (e.g., between 0.002-inch and 0.005-inch) layer of ion-sensitive glass, adapted to serve as a membrane 44 sensitive to hydrogen (or other) ions. Supporting disk 40 is a mechanically rigid substrate or matrix for supporting the membrane 44. Thus the tendency of the membrane to shatter or be damaged by physical abuse is substantially reduced relative to a conventionally known glass electrode. In the preferred embodiment, both the supporting disk 40 and membrane 44 are made of the same ion-sensitive glass material. The supporting disk 40 therefore has the same thermal expansion characteristic as the membrane 44 and the previously described limitations of the '098 patent are avoided.

Inserted through the top of glass tube 30 is the internal reference electrode element 46 (which, for example, may be a silver/silver chloride reference electrode) connected to terminal 14. The probe is immersed in a liquid electrolyte 47 to establish a stable potential at the internal surface of the glass membrane and a chloride ion solution containing excess silver-chloride to establish a stable reference potential with the internal silver/silver chloride reference element.

The glass tube 30 and the non-porous membrane 44 together form a container (or vessel) holding the electrolyte 47 in continuous contact with the supporting disk 40. The liquid electrolyte 47 flows (or seeps) down through the internal labyrinthine channels of the supporting disk 40 to make contact with the inner surface of the thin glass membrane 44. The other side of this membrane is in contact with the flowing liquid 12 thereby permitting the electrode 10 to develop in the usual fashion a potential (across membrane 44) responsive to the concentration of hydrogen ions in the liquid 12.

Electrode 10 made in accordance with one procedure can be assembled by first fusing the supporting disk 40 to the glass tube 30, and then applying the ion-sensitive glass membrane 44 over the supporting disk 40 and the exposed end surfaces of the tube. The fusion of the fritted material of this supporting disk to the cylindrical glass tube 30 can be accomplished by conventional means, such as by the localized heat of a torch, by induction heating, or by heating via infrared waves. The glass membrane 44 may be applied to supporting disk 40 in any of several ways. For example, the ion-sensitive glass may be first ground into a powdered form and mixed with an organic binder to form a liquid slurry. This slurry is spread onto the flat surface of the supporting disk to form a coating covering the entire surface of the disk and the end surface of the glass tube as well. Finally, this coated disk is heated locally to a temperature above the softening point of the glass in the slurry and thereafter allowed to cool for developing a glazed surface on the disk.

In order to insure that membrane 44 is made non-porous, the slurry must be fired to a temperature sufficient to fuse the glass particles of the slurry to one another and to cause flow of the resulting molten mass. It should be pointed out that the firing temperature to get flow is higher than that which would be used to produce a porous fritted solid. Thus, in applicant's preferred embodiment wherein disk 40 and membrane 44 are both made of the same ion sensitive glass, the molten mass resulting from the localized firing of the slurry will also melt and combine with a thin layer of the disk thereunder so that a strong bond is formed between the disk 40 and membrane 44 after cooling.

For some applications, the ion-sensitive glass 44 may advantageously be applied to supporting disk 40 (after the latter has been fused to the glass tube 30) in the form of a thin, rigid pre-formed disk or wafer, rather than a wet slurry coat. This pre-formed wafer is aligned face-to-face with the supporting disk and the interface therebetween is then heated to the working point temperature of the ion-sensitive glass by localized heating as mentioned previously. At this working point, the glass wafer and a portion of the supporting disk 40 under the wafer form a molten solution or liquid which, upon cooling, becomes a thin non-porous strongly bonded glaze on the surface of the supporting disk.

Figure 3:
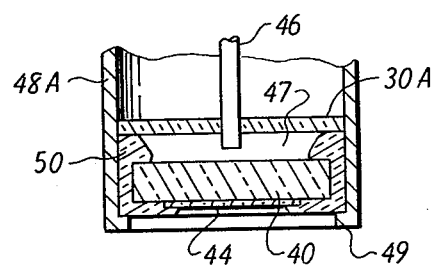
FIG. 3 is a detail section showing a modified form of construction.

The electrode 10 is preferably further provided with an outer tube 48 of tough, shock-resistant material which advantageously can be a conductive metal. With reference also to FIG. 3, the operative components of applicant's invention can all be located at the lower end of a metal tube 48A. In this alternate embodiment of the present invention, the metal tube is provided with an annular, inwardly-extending flange 49 to which is sealed the supporting disk 40 by means of a glass seal 50. The container for the electrolyte 47 is completed by a glass disk 30A fused to the glass seal 50. The glass seal 50 also is fused to supporting disk 40 (but only near the edges thereof), to the metal container (including the flange), as well as to the thin membrane 44. Thus the electrode is tightly sealed against leakage, and yet provides a rugged and relatively simple construction. Metal tube 48A and glass seal 50 used in this embodiment should have essentially the same coefficients of thermal expansion as the ion-sensitive material used for supporting disk 40 and thin membrane 44.

It should be recalled that supporting disk 40 is preferably made of the same ion-sensitive material as the membrane 44 in order to eliminate differences in the thermal expansion characteristics between those two components. However, a different material may be used for supporting disk 40 so long as that material can be made into a porous fritted solid, has a coefficient of thermal expansion substantially matching that of the ion-sensitive substance used for membrane 44, and does not hinder proper operation of the electrode. Although this different material may also be ion sensitive, such sensitivity is not a necessity thereby permitting use of other glasses or suitable materials which are less costly than ion-sensitive materials.

It should be understood that if the disk is made of a material different from the membrane, the localized firing procedure for making the membrane non-porous should be at a temperature sufficient to melt not only the ion-sensitive material of the membrane but also a thin layer of the disk thereunder. The resulting molten mass will thus contain the ion-sensitive material as well as the different material so that after cooling, a non-porous glaze-like layer is formed on and bonded to the disk.

While the present invention has been described with reference to the preferred embodiments, it will be apparent to those skilled in the art that improvements and modifications may be made within the purview of the invention without departing from the true spirit and scope thereof as defined in the appended claims.

I claim:

1. In an electrode for measuring the activity or concentration of a predetermined ion in a test solution, said electrode being of the type which includes a container holding an electrolyte in solution form and which has one wall portion thereof comprising a mechanically-stiff porous member and a relatively thin non-porous ion-sensitive membrane;

wherein said porous member is arranged to expose one surface to said electrolyte, and said membrane is arranged to expose an outer surface to said test solution and is joined to said porous member at a second surface thereof opposite said one surface, for the purpose of developing an electrical potential responsive to the activity or concentration of the predetermined ion;

that improvement in the foregoing type of electrode which comprises:

said porous member being a solid made of a material having a composition which is the same as that for said membrane, said porous member being formed by a sintering process in which particles of said membrane material are joined to form a solid having labyrinthine channels that extend randomly therethrough in all directions for carrying said electrolyte from said one surface to said second surface, and said porous member being fused to said second surface of the membrane to effect a molecular bond between said porous member and said membrane.

2. In an electrode as claimed in claim 1, further including a joining layer for bonding said membrane to said porous member, said joining layer being a solid which includes both said materials of the porous member and the membrane.

3. The electrode as claimed in claim 2, wherein said container is made of metal with said porous supporting member being sealed thereto by a glass seal;
the glass, metal and supporting member having substantially equal thermal coefficients of expansion.

4. The electrode as claimed in claim 1 wherein said electrolyte container is constructed with a cylindrical side wall and said thin membrane forms a flat bottom portion of said container.

5. The electrode as claimed in claim 4 further including a shock-resistant tubular cladding for protecting the side wall of said electrolyte container.

6. A method of making an ion-sensitive electrode, for measuring the ion activity or concentration of an industrial process fluid, comprising the steps of:
sintering together individual masses of a material sensitive to the ion of interest to form a thick, rigid, porous supporting body having non-uniform labyrinthine channels extending randomly therethrough in all directions;
fusing an ion-sensitive substance as a relatively thin, nonporous membrane to one surface of said supporting body and effecting a molecular bond between said supporting body and said membrane, wherein said ion-sensitive substance is the same as said material of said porous supporting body; and
securing said supporting body and said membrane to an electrolyte container for forming one wall portion thereof;
wherein the labyrinthine channels of said supporting body serve as paths for carrying an electrolyte therethrough to an interior surface of said membrane while the exterior surface of said membrane is in contact with the process fluid.

7. The method claimed in claim 6 further comprising the steps of:
grinding the ion-sensitive substance into a powder;
mixing the powdered substance with another material to form a liquid slurry; and
coating the porous supporting body with the liquid slurry prior to the fusing step.

8. The method as claimed in claim 6 further comprising the step of:
positioning a thin, pre-formed wafer of the ion-sensitive substance on said one surface of the porous supporting body prior to the fusing step.

9. The method of claim 6 wherein said electrolyte container includes sidewalls covered by a metal enclosure.

10. The method as claimed in claim 6 wherein said fusing step further comprises:
heating said ion-sensitive substance and a thin layer of the supporting body at said one surface thereof into a molten mass which includes in liquid form said ion-sensitive substance and said supporting body material; and
cooling said molten mass into said non-porous membrane which is bonded to said supporting body.

* * * * *